(12) United States Patent
Duckert

(10) Patent No.: US 6,442,422 B1
(45) Date of Patent: Aug. 27, 2002

(54) COMPLIANCE MONITORING APPARATUS AND METHOD

(75) Inventor: David W. Duckert, Menomonee Falls, WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/372,696

(22) Filed: Aug. 11, 1999

(51) Int. Cl.[7] ............................................... A61N 1/08
(52) U.S. Cl. ........................ 600/547; 607/62; 607/63; 128/908
(58) Field of Search ............................... 607/2, 48, 46, 607/50, 62, 63, 75, 72, 115; 600/587, 595, 547, 546, 548; 128/908

(56) References Cited

U.S. PATENT DOCUMENTS

| | | | | |
|---|---|---|---|---|
| 3,677,261 A | * | 7/1972 | Day | 128/2 |
| 4,059,169 A | * | 11/1977 | Hagen | 128/205 |
| 4,088,141 A | * | 5/1978 | Niemi | 128/422 |
| 4,116,231 A | * | 9/1978 | Matsuo | 128/2.1 |
| 4,177,799 A | * | 12/1979 | Masreliez | 128/741 |
| 4,204,545 A | * | 5/1980 | Yamakoshi | 128/693 |
| 4,372,319 A | * | 2/1983 | Ichinomiya et al. | 123/421 |
| 4,416,277 A | * | 11/1983 | Newton et al. | 128/303.13 |
| 4,468,723 A | * | 8/1984 | Hughes | 363/82 |
| RE32,091 E | * | 3/1986 | Stanton | 128/423 |
| 4,785,812 A | * | 11/1988 | Pihl et al. | 128/419 |
| 5,087,257 A | * | 2/1992 | Farin et al. | 606/35 |
| 5,800,458 A | | 9/1998 | Wingrove | 607/2 |

* cited by examiner

Primary Examiner—Kennedy Schaetzle
(74) Attorney, Agent, or Firm—Michael Best & Friedrich LLP

(57) ABSTRACT

A method and apparatus for evaluating the connection between the patient monitor and the patient. The apparatus is a compliance monitoring circuit that generates a constant current output to the isolation transformer of a patient monitoring device. Changes in the impedance of the patient connection cause changes in the output voltage of the constant current generator. This voltage can be measured and compared against a reference to generate a visible or audible compliance alarm.

25 Claims, 1 Drawing Sheet

COMPLIANCE MONITORING APPARATUS AND METHOD

BACKGROUND OF THE INVENTION

The invention relates to a patient monitor, and particularly, to a patient monitor having a compliance monitoring circuit for indicating a degradation in the connection of the patient monitor to a patient.

Compliance monitoring circuits are used in a variety of environments. In general, the term "compliance" is used to indicate the ability of a current source to match (i.e., supply current to) a changing load. The term "compliance" in the medical field is used to indicate the ability of the current source of the patient monitor to match the changing impedance of the patient connection. The electrical impedance between the medical device and the patient varies greatly depending upon patient temperature, skin moisture content, electrode adhesion, etc. In a patient monitoring device, the compliance can be monitored to provide an indication of the quality of the connection between the medical device and the patient.

One example of a compliance monitoring circuit is disclosed in U.S. Pat. No. 5,800,458 to Wingrove. Wingrove discloses using the compliance monitor as a timer in a stimulator unit for electrotherapy. As electrotherapy is being applied to a subject, the timer of the compliance monitor keeps track of the amount of time therapy is being applied. If the compliance monitor has a degrading connection to the subject (such as the subject removing the instrument), the compliance circuit will stop the timer.

Another example of a compliance monitoring circuit is in a patient monitor used for determining whether neuromuscular blocking agents in anesthesia are still active (commonly referred to as a neuromuscular monitor). Neuromuscular blocking agents are used to paralyze specific muscles of the body to allow a clinician to perform specific medical procedure such as intubation (the process of placing a tube into the patient's trachea to establish an airway), or to generally anesthetize patients during general surgical procedures. To eliminate movement of the patient, a large dose of neuromuscular blocking drug is given to completely paralyze the patient.

Depending on the amount of drug given, different degrees of neuromuscular block can be achieved. Some surgical processes require very little paralyzation while others require long periods of intense block. A commonly used method for monitoring the degree of block involves applying a small electrical current to the patient's skin (near a nerve) and noting the response of the associated muscle. Typically the current is delivered to the wrist (ulnar nerve) and the thumb moves in response. With a deep block, the thumb may not move at all; with no block, the thumb's movement is quite pronounced; and with a shallow block, the thumb's movement is decreased. A trained anesthesiologist can gauge the thumb movement by feel and adjust the administration of blocking drugs accordingly. The device which applies the stimulus is usually battery powered and delivers currents in range of 50 mA.

Problems arise, however, if the patient impedance is high or if the connection of the patient monitor to the patient is poor (e.g. if the electrode is falling off or has fallen off of the patient). If the patient impedance is high, or if the patient connection is poor, the electrical stimulus may be insufficient to generate a muscular response. Stated differently, the current source of the patient monitor may not have enough power to match the changing impedance of the patient connection. Under these circumstances, a clinician may wrongly assume an adequate state of anesthetization exists. Therefore, a compliance monitoring circuit is required to monitor the quality of the connection of the patient monitor to the patient.

SUMMARY OF THE INVENTION

Accordingly, the invention provides a patient monitor and a means for evaluating the connection between the patient monitor and the patient. The means for evaluating the connection includes a compliance monitoring circuit. The compliance monitoring circuit includes a constant current generator delivering a constant current to an isolation transformer, and a signal generator connected to the primary winding to generate a signal in response to a change in the connection to the patient. The input voltage to the constant current generator can be any type of voltage waveform including a square wave. The isolation transformer has a primary winding connected to the current generator and a secondary winding connected to a patient by electrodes. The power being supplied to the primary winding is reflected to the secondary winding at a different voltage and current. Furthermore, the impedance of the load will be reflected from the secondary winding to the primary winding.

The signal generator of the compliance monitoring circuit further includes alarm signal circuitry connected to the constant current generator. The alarm signal circuitry provides an alarm signal to indicate when there is a degradation in the connection of the electrode to the patient or where one of the electrodes is accidentally removed or otherwise becomes disconnected. This will result in a high or even infinite load resistance The invention further provides a method for monitoring the compliance of a connection between a patient monitoring device and a patient. The monitoring of the compliance includes the acts of providing an isolation transformer connected between the patient monitor and the electrode, generating a constant current in the primary winding using a constant current generator connected to the primary winding, monitoring the compliance voltage of the constant current generator to determine compliance of the connection between the electrode and the patient, and generating a signal in response to a change in the connection to the patient.

In one embodiment, the monitoring of the compliance voltage includes the act of generating a signal, which may be used as an alarm signal, to indicate a degradation in the connection between the electrode and the patient. In still another embodiment, the monitoring of the compliance voltage also includes the act of comparing the compliance voltage to a reference voltage. If the compliance voltage is greater than the reference voltage, the alarm signal will be generated.

It is a principal advantage of the invention to provide a patient monitor and a compliance alarm circuit therefor for measuring the load on the secondary without the use of complex circuitry.

It is another advantage of the invention to provide a patient monitor and a compliance monitor therefor that generates a signal, which may be used as an alarm signal, when there is degradation in the connection of the compliance monitoring circuit or patient monitor to the patient.

It is another advantage of the invention to provide a patient monitor and a compliance alarm circuit therefor that takes advantage of the isolation transformer's ability to reflect the impedance of the load from the secondary winding to the primary winding.

It is another advantage of the invention to provide a method of measuring the compliance of a connection between an electrode of a patient monitoring device and a patient by monitoring a compliance voltage of a constant current generator.

It is another advantage of the invention to provide a method of measuring the compliance of a connection between an electrode of a patient monitoring device and a patient by generating a signal, which may be used as an alarm signal to indicate a when a degradation in the connection between the electrode and the patient.

Other features and advantages of the invention will become apparent to those skilled in the art upon review of the following detailed description, claims, and drawings.

DETAILED DESCRIPTION OF THE PREFERRED EMBODIMENT

Figure 1:
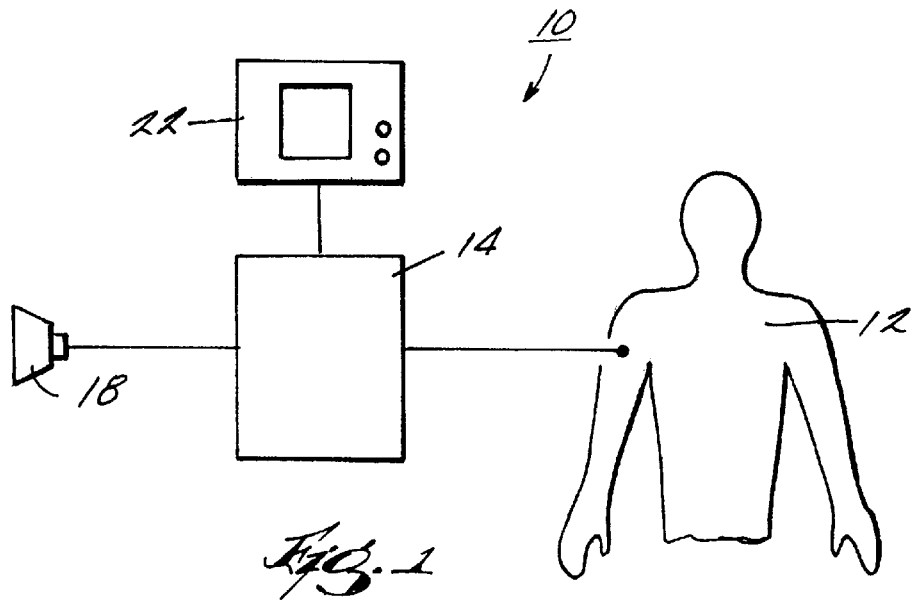
FIG. 1 illustrates a patient and a patient monitor embodying the invention connected to the patient.

Shown in FIG. 1 of the drawings is a patient monitor 10 embodying the invention. While the invention is applicable to any patient monitoring device that requires an electrical connection to the patient 12, the patient monitor 10 of the preferred embodiment is a neuromuscular monitor. As shown in FIG. 1, the neuromuscular monitor includes a central processing unit 14, a display device 18 and a speaker 22. The display device 18 and speaker 22 provide visible and audible indications, respectively, of the condition of the patient, and provide other information relating to the quality of the connection between the patient monitor and the patient.

Figure 2:
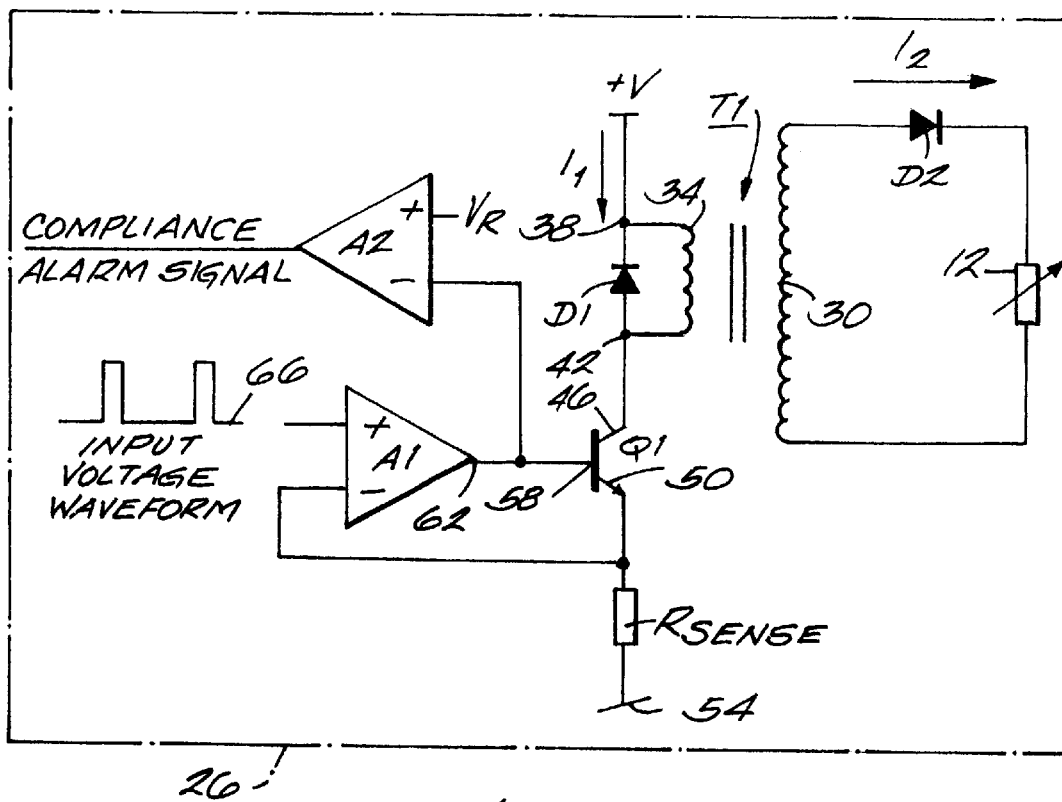
FIG. 2 illustrates the compliance monitoring circuit of the patient monitor.

As shown in FIG. 2, the patient monitor 10 includes a compliance alarm circuit 26. The patient 12 is represented as a variable resistance and is connected to the neuromuscular monitor using appropriate electrodes (not shown). One of the electrodes is connected to the secondary 30 of a patient isolation transformer T1 through diode D2 and the other electrode is connected to the opposite end of the secondary 30 of the patient isolation transformer T1. The patient isolation transformer T1 includes a primary winding 34 having positive and negative terminals, 38 and 42, respectively. The primary winding 34 of the patient isolation transformer T1 is connected in parallel with diode D1. The positive terminal 38 of the primary winding is connected to a voltage source (+V) and the negative terminal 42 is connected to the collector 46 of transistor Q1. The emitter 50 of transistor Q1 is connected to ground 54 through a sensing resistor $R_{sense}$. The base 58 of transistor Q1 is connected to the output 62 of an operational amplifier A1. The operational amplifier Al is connected in a closed-loop configuration such that the inverting input (−) of operational amplifier Al is connected to the emitter 50 of transistor Q1. The non-inverting input (+) of operational amplifier Al is connected to a voltage source 66. In the preferred embodiment, the voltage source 66 is a square wave input voltage waveform. In this configuration, the operational amplifier A1 and transistor Q1 form a constant current source for the patient monitor 10.

The compliance alarm circuit also includes a comparator connected to the output of operational amplifier A1 to generate a compliance alarm signal. The comparator includes operational amplifier A2, which has an inverting input (−) connected to the output of operational amplifier A1 and a non-inverting input (+) connected to a voltage reference.

In operation, the electrode (not shown) connected to the secondary winding is connected to the patient 12 and an input voltage 66 is applied to the non-inverting input (+) of operational amplifier A1. The input voltage waveform results in a current output that biases transistor Q1. Assuming that the input voltage waveform is 2 volts at its peak, the operational amplifier A1 will sink or source current as necessary to keep the inverting and non-inverting input terminals at the same 2 volt potential. For example, if the sense resistor impedance is 1 ohm and the voltage at the non-inverting input (+) of operational amplifier A1 is equal to 2 volts, then the operational amplifier will sink or source current in an attempt to keep the input voltage at the inverting input (−) of operational amplifier A1 at 2 volts. This of course means that the voltage at the emitter of transistor Q1 is 2 volts. Since the impedance of sense resistor $R_{SENSE}$ is 1 ohm, the current through the sense resistor $R_{SENSE}$ is 2 volts/1 ohm=2 amps (the current through the base of the transistor is negligible and is ignored for this calculation). This current is represented as arrow $I_1$ in FIG. 2.

The isolation transformer T1 transforms the low voltage, high constant-current waveform ($I_1$) into a high-voltage, low constant-current waveform ($I_2$) on the secondary winding 30 of the isolation transformer T1. The isolation transformer T1 also provides the necessary patient isolation barrier to protect the patient 12 from exposure to undesired electrical currents. The current ($I_2$) is supplied to the patient 12. The impedance of the patient 12 is reflected to the primary 34 of the isolation transformer T1 as a load resistance. If the impedance of the patient becomes too high, the constant current source will exceed its ability to generate current to accommodate the high impedance of the patient 12. As a result, the output of operational amplifier A1 will saturate at its upper supply of voltage.

For example, assume that the supply voltage (+V) is 10 Volts and the impedance of the patient 12 is 1000 ohms. Also assume that the resistor $R_{sense}$ is 1 ohm and that the winding ratio of the transformer T1 is 1:50. If a 2 Volt DC input voltage waveform 66 is applied, a constant current of 2 amps (A) will be developed through the primary winding 34 of the transformer (2 Volts /1 ohm=2 A). A 0.040 A isolated constant current will develope in the secondary of the transformer 30 (2 A/50 winding ratio=0.04 A) and this current is applied to the patient.

The patient impedance is reflected through the transformer T1 and results in a transformer primary winding impedance of 0.4 ohms (1000 ohms /$50^2$ winding ratio=0.4 ohms). The voltage drop across the transformer primary winding 34 will be 0.8 volts (0.4 ohms×2 A=0.8 volts). The drop across the resistor $R_{sense}$ will be 2 volts (1 ohm×2A=2 volts). Since the supply voltage is 10 volts, transistor Q1 will drop the remaining 7.2 volts (10 volts−0.8 volts−2 volts=7.2 volts) to remain in the linear region of operation and control the primary current. The base 58 of the transistor will operate at a point of about 2.7 volts (2 volts across $R_{sense}$+ 0.7 volts B−E drop=2.7 volts).

Now assume that the patient connection degrades so that the patient impedance is now 10,000 ohms. This impedance is too great for the constant current source to continue to supply the same level of current to the load, i.e., the patient. The patient impedance is reflected through the transformer T1 and results in a transformer primary impedance of 4 ohms (10,000 ohms /$50^2$ winding ratio=4 ohms). The voltage drop across the transformer primary 34 will be 8 volts (4 ohms×2 A=8 volts). The drop across the resistor $R_{sense}$ will 2 volts (1 ohm×2A=2 volts). The sum of these two voltage drops is 10 volts, and since the supply voltage is only 10 volts, transistor Q1 is unable to remain in the linear region of control.

Essentially, the circuit has "run out" of voltage such that the constant current source cannot comply with the demand. In the situation where the load is too high, operational amplifier A1 attempts to source current to the load causing the output voltage of operational amplifier A1 to rise from its stable operating point of approximately 2.7 volts to the maximum output voltage of the operational amplifier A1. This rise is easily measured and can be used to detect when the current source reaches its limit of ability to provide a constant current to the load. Stated differently, the output of operational amplifier A1 is fed to the operational amplifier A2 and is compared against the reference voltage (VR). When the voltage of the output of operational amplifier A1 exceeds the reference voltage (VR), a compliance alarm signal is generated to indicate that something is wrong with the patient connection. The alarm generated can either be an audible or a visible alarm depending upon the needs of the clinician.

In summary, the method of monitoring the compliance of a connection between an electrode of a patient monitoring device and the patient includes the acts of providing and isolation transformer connected between the patient monitor and the electrode. The isolation transformer includes a primary winding and a secondary winding. The patient monitor then generates a constant current in the primary winding using a constant current generator connected to the primary winding and monitors the compliance voltage of the constant current generator to evaluate the connection between the electrode and the patient. In response to an increase in the compliance voltage beyond a reference voltage, the patient monitor generates an alarm signal to indicate a degradation in the connection between the electrode and the patient.

Before one embodiment of the invention is explained in detail, it is to be understood that the invention is not limited in its application to the details of construction and to arrangements of components set forth in the following description of illustrated in the drawings. The invention is capable of other embodiments and is capable of being practiced or of being carried out in various ways. Also, it is to be understood that the phraseology and terminology used herein is for the purpose of description and should not be regarded as limiting.

Various features and advantages of the invention are set forth in the following claims.

What is claimed is:

1. A compliance monitoring circuit for evaluating a connection between a patient monitor and a patient, the compliance monitoring circuit comprising:
    a constant current generator delivering a constant current output, the constant current generator including circuitry that attempts to comply with a reflected impedance of the connection;
    an isolation transformer having a primary winding connected to the constant current generator so as to receive the constant current output, and having a secondary winding for connection to the patient;
    a signal generator connected to the primary winding to generate a signal in response to a change in the connection to the patient; and
    wherein the signal generator comprises:
        alarm signal circuitry connected to the constant current generator, the alarm signal circuitry providing an alarm signal to indicate a degradation in the connection to the patient.

2. A compliance monitoring circuit as set forth in claim 1, wherein a supply voltage is connected to a first end of the primary winding and the constant current generator comprises:
    an operational amplifier having a non-inverting input receiving an input signal, an inverting input, and an output;
    a transistor having a base connected to the output of the operational amplifier, a collector connected to a second end of the primary winding, and an emitter connected to the inverting input of the operational amplifier;
    a resistor having a first end connected to the emitter and a second end connected to a floating reference;
    wherein the operational amplifier, transistor and resistor attempt to comply with the impedance of the patient connection; and
    wherein the alarm signal circuitry is connected to the base of the transistor.

3. A compliance monitoring circuit as set forth in claim 2, the alarm signal circuitry comprising:
    a comparator, the comparator having a first input connected to the base of the transistor, a second input connected to a reference voltage, and an output providing the alarm signal.

4. A compliance monitoring circuit as set forth in claim 2, wherein the alarm signal circuitry provides the alarm signal when the operational amplifier, transistor and resistor fail to comply with the impedance of the patient connection.

5. A compliance monitoring circuit as set forth in claim 2, wherein the secondary winding is connected in series to a diode.

6. A compliance monitoring circuit as set forth in claim 2, wherein the primary winding is connected in parallel to a diode.

7. A compliance monitoring circuit as set forth in claim 2, wherein the alarm signal circuitry provides the alarm signal when the circuitry fails to comply with the impedance of the connection.

8. A patient monitor including a compliance monitoring circuit for evaluating a connection between the patient monitor and a patient, the compliance monitoring circuit comprising:
    a constant current generator delivering a constant current output, the constant current generator including circuitry that attempts to comply with an impedance of the patient connection;
    an isolation transformer having a primary winding connected to the constant current generator so as to receive the constant current output, and having a secondary winding for connection to the patient; and
    a signal generator connected to the primary winding to generate a signal in response to a change in the connection to the patient;
    wherein the signal generator comprises:
        alarm signal circuitry connected to the constant current generator, the alarm signal circuitry providing an alarm signal to indicate a degradation in the connection to the patient.

9. A patient monitor as set forth in claim 8, wherein a supply voltage is connected to a first end of the primary winding and the constant current generator comprises:

an operational amplifier having a non-inverting input receiving an input signal, an inverting input, and an output;

a transistor having a base connected to the output of the operational amplifier, a collector connected to a second end of the primary winding, and an emitter connected to the inverting input of the operational amplifier;

a resistor having a first end connected to the emitter and a second end connected to a floating reference;

wherein the operational amplifier, transistor and resistor attempt to comply with the impedance of the patient connection; and wherein the alarm signal circuitry is connected to the base of the transistor.

10. A patient monitor as set forth in claim 9, wherein the alarm signal circuitry provides the alarm signal when the operational amplifier, transistor and resistor fails to comply with the impedance of the patient connection.

11. A patient monitor as set forth in claim 9, the alarm signal circuitry comprising:

a comparator, the comparator having a first input connected to the base of the transistor, a second input connected to a reference voltage, and an output, the output provides the alarm signal.

12. A patient monitor as set forth in claim 8, wherein the secondary winding is connected in series to a diode.

13. A patient monitor as set forth in claim 8, wherein the primary winding is connected in parallel to a diode.

14. A patient monitor as set forth in claim 8, further comprising at least one electrode connected to the secondary winding.

15. A patient monitor as set forth in claim 8, wherein the alarm signal circuitry provides the alarm signal when the circuitry fails to match the impedance of the patient connection.

16. A patient monitor for measuring a physiological parameter of a patient connected to the patient monitor, the patient monitor comprising:

an electrode connectable to the patient;

means for measuring a compliance of a constant current applied to the electrode when the electrode is connected to the patient;

a signal generator connected to the measuring means to generate a signal in response to a lack of compliance; and wherein the measuring means includes a constant current generator attempting to comply the constant current to an impedance of the connection.

17. A patient monitor as set forth in claim 16 wherein the means for measuring the compliance of the connection between the electrode and the patient includes an isolation transformer having a primary winding connected to the constant current generator so as to receive the constant current, and having a secondary winding for connection to the patient.

18. A patient monitor as set forth in claim 19, wherein the means for measuring the compliance of the connection between the electrode and the patient includes a supply voltage connected to a first end of the primary winding and the constant current generator comprises:

an operational amplifier having a non-inverting input receiving an input signal, an inverting input, and an output;

a transistor having a base connected to the output of the operational amplifier and to the alarm signal circuitry, a collector connected to a second end of the primary winding, and an emitter connected to the inverting input of the operational amplifier;

a resistor having a first end connected to the emitter and a second end connected to a floating reference; and wherein the operational amplifier, transistor and resistor attempt to comply with the impedance of the patient connection.

19. A patient monitor as set forth in claim 18, wherein the means for measuring the compliance of the connection between the electrode and the patient includes a diode connected in series with the secondary winding.

20. A patient monitor as set forth in claim 18, wherein the means for measuring the compliance of the connection between the electrode and the patient includes a diode connected in parallel to with the primary winding.

21. A patient monitor as set forth in claim 18, the alarm signal circuitry comprising a comparator, the comparator having a first input connected to the base of the transistor, a second input connected to a reference voltage, and an output, the output provides the alarm signal.

22. A patient monitor as set forth in claim 18, wherein the signal generator provides the signal when the operational amplifier, transistor and resistor fail to comply with the impedance of the patient connection.

23. A patient monitor as set forth in claim 16, wherein the signal generator generates the signal when the measuring means fails to match the impedance of the patient connection.

24. A method of monitoring the compliance of a connection between an electrode of a patient monitoring device and a patient, the method comprising the acts of:

providing an isolation transformer connected between the patient monitor and the electrode, the isolation transformer including a primary winding and a secondary winding;

generating a constant current in the primary winding using a constant current generator connected to the primary winding, attempting to comply the constant current with an impedance of the connection;

monitoring a compliance voltage of the constant current generator to evaluate the connection between the electrode and the patient; and generating a signal in response to failing to generate a constant current.

25. The method as set forth in claim 24, wherein the monitoring of the compliance voltage includes the act of comparing the compliance voltage to a reference voltage.

* * * * *